United States Patent [19]

Mills et al.

[11] Patent Number: 4,973,470

[45] Date of Patent: Nov. 27, 1990

[54] SUSTAINED RELEASE PHARMACEUTICAL COMPOSITIONS

[75] Inventors: Nancy L. Mills, Mount Arlington; Michael R. Harris, Hackettstown; Russell U. Nesbitt, Somerville, all of N.J.

[73] Assignee: Warner-Lambert Company, Ann Arbor, Mich.

[21] Appl. No.: 371,524

[22] Filed: Jun. 26, 1989

[51] Int. Cl.[5] ............................................. A61K 9/20
[52] U.S. Cl. ..................................... 424/467; 424/468
[58] Field of Search ................................ 424/467, 468

[56] References Cited

U.S. PATENT DOCUMENTS

| | | | |
|---|---|---|---|
| 2,395,881 | 7/1969 | Hamada | 167/82 |
| 3,133,863 | 5/1964 | Tansey | |
| 3,758,679 | 9/1973 | Seidler | 424/19 |
| 3,773,920 | 11/1973 | Nakamoto et al. | 424/19 |
| 4,547,358 | 10/1985 | David et al. | 424/467 |
| 4,556,678 | 12/1985 | Hsiao | 514/652 |
| 4,590,062 | 5/1986 | Jang | 424/19 |
| 4,652,442 | 3/1987 | Hopfgartner et al. | 514/420 |
| 4,786,508 | 11/1988 | Ghebre-Sellassie et al. | 424/482 |

*Primary Examiner*—Thurman K. Page
*Attorney, Agent, or Firm*—Mathews, Woodbridge & Collins

[57] ABSTRACT

A sustained release oral pharmaceutical composition consists essentially of a recompressed mixture of a water-sensitive pharmaceutical agent, a high molecular weight hydrophilic cellulose polymer, and a lubricant. The mixture is compressed into a unitary mass, comminuted, and recompressed into tablets without the use of solvents.

1 Claim, No Drawings

SUSTAINED RELEASE PHARMACEUTICAL COMPOSITIONS

The present invention pertains to a pharmaceutical composition having sustained release properties which is suitable for use with water-sensitive pharmaceutical agents, and to the method of formulating such compositions.

BACKGROUND OF THE INVENTION

Numerous sustained released formulations have been described in the literature. Many of these rely on structural features such as enteric coatings, coated core particles, or matrix structures.

The use of high molecular weight hydrophilic cellulose polymers to impart sustained or controlled release also has been described previously. Typical hydrophilic cellulose polymers used for this purpose include sodium carboxymethylcellulose, hydroxypropylcellulose, hydroxypropylmethylcellulose, and hydroxyethylcellulose.

Generally, the use of such high molecular weight hydrophilic cellulose polymers to impart sustained or controlled release has relied upon formulations in which up to about 10% of polymer is admixed with an excipient such as lactose. The formulation is wet granulated and then compressed into tablets. Upon coming in contact with an aqueous medium, the polymer on the outer surface is hydrated, forming a gel layer through which water then permeates. In the case of a formulation of a water soluble drug, the active ingredient diffuses out through the gel layer. If the drug is water-insoluble, it is released through erosion.

U. S. Pat. No. 3,758,679 describes a process in which a granulating agent such as sodium carboxymethylcellulose, methylcellulose, hydroxypropylmethylcellulose and the like is granulated with water and then extruded to produce time-released particles.

U.S. Pat. No. 4,556,678 describes the granulation of hydroxypropylmethylcellulose and hydroxypropylcellulose with water and isopropanol to form granules which then are compressed into tablets.

Wet granulation techniques are recognized as being unsuitable for water sensitive drugs. U.S. Pat. No. 4,652,442, for example, describes a granulation technique in which a kneadable dough is formed from hydrophilic cellulose polymers and organic solvents such as ethanol, propanol, or acetone. Similar approaches using organic solvents are disclosed in U.S. Pat. Nos. 3,133,863 and 3,773,920.

U.S. Pat. No. 2,395,881 discloses a process in which ethyl cellulose is heated with an oil and a molten mixture of the therapeutic agent (quinidine gluconate) is then granulated with minimal isopropanol.

To avoid the use of both water and organic solvents, U.S. Pat. No. 4,590,062 describes a dry, direct compressed tablet in which a cellulosic material is admixed with "digestive-difficulty soluble component" such as a wax, lipid, or oil.

Direct compression of cellulose polymers has been explored but often produces a tablet of insufficient hardness. This may be a result of the recognized fact that cellulose polymers are themselves not particularly good binders. Moreover because the cellulose polymers are very fine in particle size, they do not lend themselves to particle flow and do not produce a good flowing tablet formulation for direct compression.

DETAILED DESCRIPTION

The present invention pertains to a sustained release oral pharmaceutical composition of a water-sensitive pharmaceutical agent and a high molecular weight hydrophilic cellulose polymer which is directly compressible and which requires no solvents or binders. In particular, the invention is based on the discovery that if the mixture of the water-sensitive pharmaceutical agent and high molecular weight hydrophilic cellulose polymer, together with a lubricating amount of a pharmaceutical lubricant, is first compressed into a unitary mass and then comminuted, the resultant tablets formed upon recompression of the comminuted precompressed mixture will have adequate hardness and sustained release properties.

Preferably the water-sensitive pharmaceutical agent and high molecular weight cellulose polymer together constitute at least 95%, most preferably 99%, of the weight of the pharmaceutical composition. Although not so limited, the formulation is particularly suitable of high dose pharmaceutical agents since the absence of the need for other adjuvants permits the formulations in which the pharmaceutical agent constitutes 50% or more of the weight of the pharmaceutical composition.

The high molecular weight cellulose polymer can be methylcellulose, sodium carboxymethylcellulose, hydroxypropylcellulose, hydroxypropylmethylcellulose, hydroxyethylcellulose, and the like. It will be appreciated that these are available commercially (under a number of trademarks including KLUCEL, NATROSOL, METHOCEL, AQUALON, etc.). Preferably the high molecular weight cellulose polymer is hydroxypropylmethylcellulose or hydroxyethylcellulose.

Pharmaceutical agents which are water-sensitive have a variety of pharmacological indications. Typical of this type of agent are quinapril HCl, procaterol HCl hemihydrate, enalapril maleate, pramiracetam sulfate, quinidine gluconate, and acetylsalicylic acid, to exemplify but a few. For purposes of illustration, N-acetylprocainamide, a procainamide derivative having antiarrhythmic properties, will be used herein as a typical embodiment of the present invention. N-Acetylprocainamide thus reflects the type of drug for which the present invention is particularly well-suited since it is water-sensitive and has a mean half-life of about 7–8-hours, being repeatedly administered in a relatively high dose of 1 to 2.5 grams every 6 to 8 hours.

Suitable lubricants include magnesium stearate, calcium stearate, zinc stearate, stearic acid, hydrogenated vegetable oil, hydrogenated soybean oil, talc, and polyethylene glycol (6000–8000). Since the only function of this component is to provide conventional lubrication, it need be present only in an amount sufficient to provide such lubrication; e.g., 0.5 to 2%.

According to the present invention, the water-sensitive pharmaceutical agent in an amount sufficient to provide a therapeutically effective dose in the final composition and one or more high molecular weight hydrophilic cellulose polymers, together with at least a lubricating amount of the lubricant, are mixed. Typically the high molecular weight hydrophilic cellulose polymers will be present in an amount of 10% or more by weight of the final composition with the balance (other than the lubricant) constituting 50 to 90% by weight or more of the final composition. A typical composition contains about 15% of high molecular weight hydrophilic cellulose polymer and about 85% of water-sensitive pharmaceutical agent, either or both of which percentages can be adjusted downwards to accommodate the lubricant.

The mixture of the water-sensitive pharmaceutical agent, high molecular weight hydrophilic cellulose polymer, and lubricant next is compacted into a unitary mass. The precompression can be achieved using for example a roller compressor such as a Fitzpatrick chilsonater. The unitary mass thus produced will be in the form of moderately hard waffles or compacts.

The unitary mass next is comminuted as for example by milling the compacted mixture. After relubricating the milled compacted mixture by addition of a lubricant of the type discussed above, the milled compacted mixture is compressed into tablets.

All of the processing steps are conducted without the addition of a solvent, including water.

The following examples will serve to further typify the nature of this invention but should not be construed as a limitation on the scope of the invention which is defined solely by the appended claims.

EXAMPLE 1

| Ingredient | Amount |
|---|---|
| 1. N-Acetylprocainamide | 1000.00 g |
| 2. Hydroxyethylcellulose (Natrosol 250H) | 178.50 g |
| 3. Calcium Stearate | 11.50 g |

A simple dry mix of the above ingredients was prepared and precompressed on a Fitzpatrick chilsonater utilizing circumferential sine wave grooving rollers with a roller speed of 3.5 rpm, a gap setting of 0.015 inch, and an air pressure of 35 lbs. The moderately hard waffles or compacts thereby produced were milled in a Fitzmill with a No. 2AA screen at slow speed with knives forward and relubricated with 10.00 g. of calcium stearate. The milled compacted mixture then was compressed into tablets on a Betapress without precompression to a hardness of 10–11 Kp with a gauge of 0.318–0.322 inches.

When evaluated for their release rate in 0.1N hydrochloric acid in USP apparatus 2 at 75 rpm, the following dissolution pattern was observed for the formulation of this example.

| Hours | % Released |
|---|---|
| 1 | 18.8 |
| 2 | 28.8 |
| 4 | 44.2 |
| 6 | 56.4 |
| 8 | 67.3 |
| 10 | 76.0 |
| 12 | 87.8 |

In contrast, conventional N-acetylprocainamide tablets typically are fully dissolved after 30 minutes using the above condition.

EXAMPLE 2

Tablets were prepared according to the procedure of Example 1, employing, however, hydroxypropylmethylcellulose (Methocel E4M) in place of hydroxyethylcellulose.

When evaluated for their release rate in 0.1N hydrochloric acid in USp apparatus 2 at 75 rpm, the following dissolution pattern was observed for the formulation of this example.

| Hours | % Released |
|---|---|
| 1 | 21.6 |
| 2 | 33.9 |
| 4 | 56.4 |
| 6 | 72.3 |
| 8 | 81.3 |
| 10 | 89.0 |
| 12 | 92.4 |

What is claimed is:

1. A method for preparing a sustained release oral pharmaceutical composition consisting essentially of a compressed, dry granulated mixture of a therapeutically effective amount of a water-sensitive pharmaceutical agent, a high molecular weight hydrophilic cellulose polymer, and at least a lubricating amount of a lubricant, which comprises compressing said mixture into a unitary mass, comminuting the compressed mixture, relubricating the comminuted compressed mixture, and recompressing the relubricated milled compressed mixture into tablets.

* * * * *